(12) United States Patent
Zhao

(10) Patent No.: US 12,228,302 B2
(45) Date of Patent: Feb. 18, 2025

(54) HVAC PERFORMANCE MONITORING METHOD

(71) Applicant: Carrier Corporation, Palm Beach Gardens, FL (US)

(72) Inventor: Nan Zhao, Cambridge, MA (US)

(73) Assignee: CARRIER CORPORATION, Palm Beach Gardens, FL (US)

( * ) Notice: Subject to any disclaimer, the term of this patent is extended or adjusted under 35 U.S.C. 154(b) by 366 days.

(21) Appl. No.: 17/772,896

(22) PCT Filed: Oct. 20, 2020

(86) PCT No.: PCT/US2020/056491
§ 371 (c)(1),
(2) Date: Apr. 28, 2022

(87) PCT Pub. No.: WO2021/086684
PCT Pub. Date: May 6, 2021

(65) Prior Publication Data
US 2023/0011020 A1     Jan. 12, 2023

Related U.S. Application Data

(60) Provisional application No. 62/928,397, filed on Oct. 31, 2019.

(51) Int. Cl.
*F24F 11/63* (2018.01)
*F24F 11/52* (2018.01)
(Continued)

(52) U.S. Cl.
CPC .............. *F24F 11/63* (2018.01); *F24F 11/52* (2018.01); *G16H 40/67* (2018.01); *G16H 50/30* (2018.01);
(Continued)

(58) Field of Classification Search
CPC ........ F24F 11/63; F24F 11/52; F24F 2120/14; F24F 2120/20; F24F 2110/00;
(Continued)

(56) References Cited

U.S. PATENT DOCUMENTS 5,170,935 A    12/1992   Federspiel et al.
2003/0096572 A1   5/2003   Gutta
(Continued)

FOREIGN PATENT DOCUMENTS

EP    0415747 A2   3/1991
EP    2363657 A2   9/2011
(Continued)

OTHER PUBLICATIONS

International Search Report for Application No. PCT/US2020/056491; Issued Jan. 22, 2021; 6 Pages.
(Continued)

*Primary Examiner* — Christopher W Carter
(74) *Attorney, Agent, or Firm* — CANTOR COLBURN LLP

(57) ABSTRACT

A method of monitoring performance of a building system to control ambient conditions within the interior of a structure including: detecting a physiological condition of an individual within the interior of the structure; detecting an ambient condition within the interior of the structure; determining a user activity that is assigned to an area within the interior of the structure where the individual is located; and determining a wellness performance score of the area in response to at least the physiological condition, the ambient condition, and the user activity that is assigned to an area within the interior of the structure where the individual is located.

11 Claims, 5 Drawing Sheets

(51) Int. Cl.
*G16H 40/67* (2018.01)
*G16H 50/30* (2018.01)
*F24F 120/14* (2018.01)
*F24F 120/20* (2018.01)

(52) U.S. Cl.
CPC ....... *F24F 2120/14* (2018.01); *F24F 2120/20* (2018.01)

(58) Field of Classification Search
CPC .. F24F 11/30; F24F 11/56; F24F 11/64; F24F 11/88; F24F 2120/10; G16H 40/67; G16H 50/30
See application file for complete search history.

(56) References Cited

U.S. PATENT DOCUMENTS

| | | | | |
|---|---|---|---|---|
| 2011/0276565 A1* | 11/2011 | Zheng | ................... | H04W 4/029 |
| | | | | 707/E17.084 |
| 2018/0330811 A1* | 11/2018 | Macary | .............. | G06Q 10/0639 |
| 2018/0347845 A1* | 12/2018 | Harvey | .................... | F24F 11/63 |
| 2021/0375440 A1* | 12/2021 | Schlameuss | ........... | G01N 33/18 |

FOREIGN PATENT DOCUMENTS

| | | |
|---|---|---|
| WO | 2019046580 A1 | 3/2019 |
| WO | 2019087538 A1 | 5/2019 |
| WO | 2019144937 A1 | 8/2019 |

OTHER PUBLICATIONS

Written Opinion for Application No. PCT/US2020/056491; Issued Jan. 22, 2021; 8 Pages.

* cited by examiner

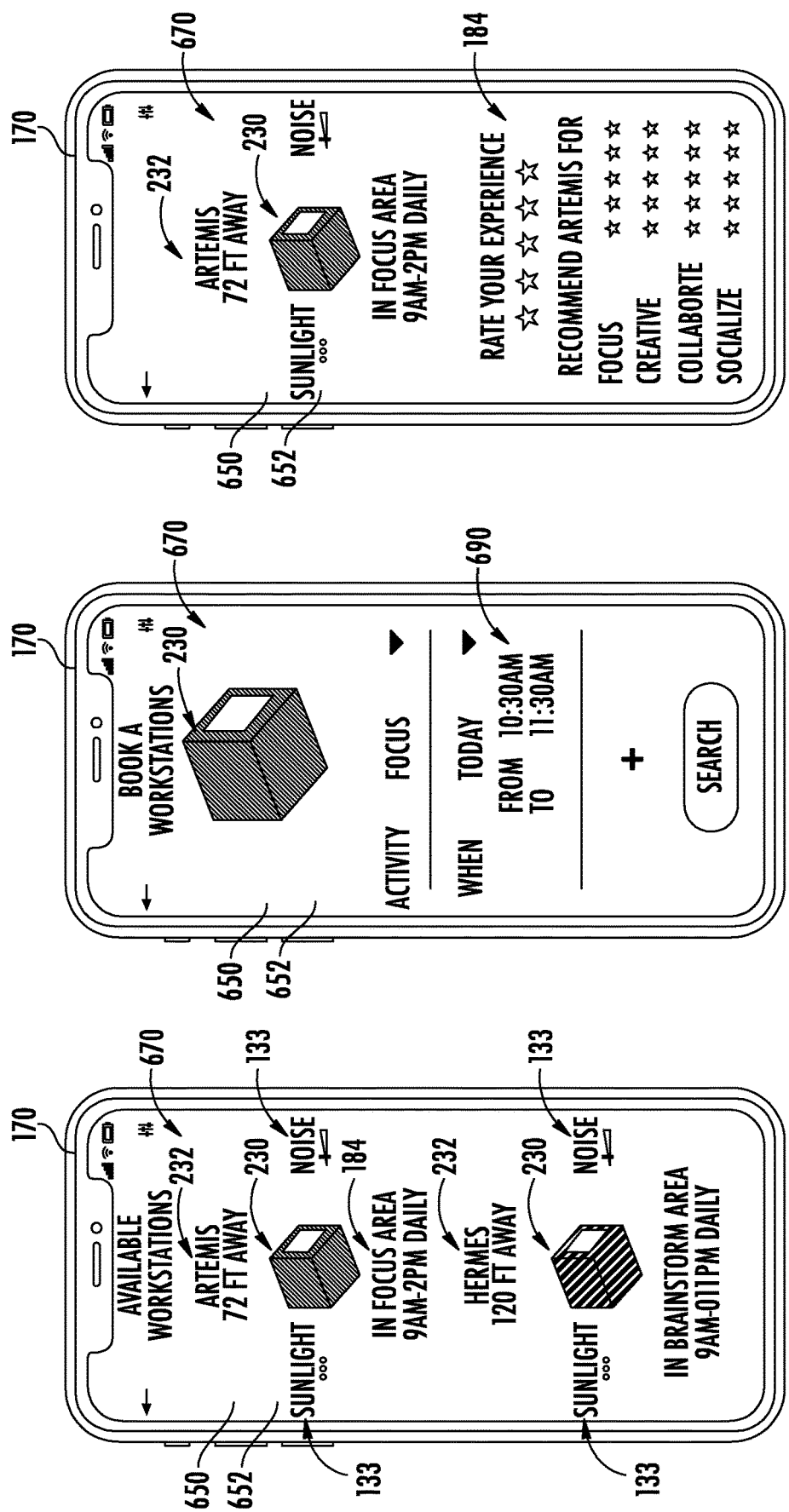

HVAC PERFORMANCE MONITORING METHOD

CROSS-REFERENCE TO RELATED APPLICATIONS

This application is a 371 U.S. National Stage application of PCT/US2020/056491, filed Oct. 20, 2020, which claims the benefit of U.S. Provisional Application No. 62/928,397, filed Oct. 31, 2019, both of which are incorporated by reference in their entirety herein.

BACKGROUND

The subject matter disclosed herein generally relates to the field of building systems, and more particularly to an apparatus and method for evaluating building systems.

Human physiological response regulates the heat balance by removing body heat generated by metabolism through various means. Some existing climate control systems employ space sensors at predefined locations in space within the building premises. The actual human thermal comfort perception may not be in line with temperature figures given by these 'fixed location' space sensors. So these space sensors do not reflect the comfort felt by the individuals.

BRIEF SUMMARY

According to one embodiment, a method of monitoring performance of a building system to control ambient conditions within the interior of a structure is provided. The method including: detecting a physiological condition of an individual within the interior of the structure; detecting an ambient condition within the interior of the structure; determining a user activity that is assigned to an area within the interior of the structure where the individual is located; and determining a wellness performance score of the area in response to at least the physiological condition, the ambient condition, and the user activity that is assigned to an area within the interior of the structure where the individual is located.

In addition to one or more of the features described above, or as an alternative, further embodiments may include: adjusting operation of the building system in response to the wellness performance score.

In addition to one or more of the features described above, or as an alternative, further embodiments may include: receiving a user rating from the individual for the area within the interior of the structure where the individual is located, wherein the wellness performance score of the area is determined in response to at least the user rating, the physiological condition, the ambient condition, and the user activity that is assigned to an area within the interior of the structure where the individual is located.

In addition to one or more of the features described above, or as an alternative, further embodiments may include: adjusting operation of the building system in response to the wellness performance score.

In addition to one or more of the features described above, or as an alternative, further embodiments may include that the physiological condition is detected using a wearable physiological sensor worn by the individual.

In addition to one or more of the features described above, or as an alternative, further embodiments may include that the physiological condition is detected using a physiological sensor configured to remotely detect the physiological conditions.

In addition to one or more of the features described above, or as an alternative, further embodiments may include: displaying the wellness performance score on a display device.

According to another embodiment, a method of monitoring performance of a building system to control ambient conditions within the interior of a structure is provided. The method including: detecting a physiological condition of one or more individuals within the interior of the structure, each of the one or more individuals being located in one or more areas of the interior; detecting an ambient condition within each of the one or more areas of the interior of the structure; determining a user activity for each of the one or more areas within the interior of the structure; determining a wellness performance score for each of the one or more areas in response to at least the physiological condition, the ambient condition, and the user activity that is assigned to an area within the interior of the structure where the individual is located; receiving a location suggestion request from an individual, the location suggestion request including a desired user activity for the individual to perform in the interior; and determining at least one area of the one or more areas for the individual in response to the desired user activity, the wellness performance score for each of the one or more areas, and the user activity for each of the one or more areas within the interior of the structure.

In addition to one or more of the features described above, or as an alternative, further embodiments may include: adjusting operation of the building system in response to the wellness performance score.

In addition to one or more of the features described above, or as an alternative, further embodiments may include: receiving a user rating from at least one of the one or more individuals for at least one of the one or more areas within the interior of the structure, wherein the wellness performance score of the at least one area of the one or more areas is determined in response to at least the user rating, the physiological condition, the ambient condition, and the user activity that is assigned to an area within the interior of the structure where the individual is located.

In addition to one or more of the features described above, or as an alternative, further embodiments may include: adjusting operation of the building system in response to the wellness performance score.

In addition to one or more of the features described above, or as an alternative, further embodiments may include that the physiological condition is detected using a wearable physiological sensor worn by the individual.

In addition to one or more of the features described above, or as an alternative, further embodiments may include that the physiological condition is detected using a physiological sensor configured to remotely detect the physiological conditions.

In addition to one or more of the features described above, or as an alternative, further embodiments may include: displaying the wellness performance score on a display device.

According to another embodiment, a computer program product embodied on a non-transitory computer readable medium is provided. The computer program product including instructions that, when executed by a processor, cause the processor to perform operations including: detecting a physiological condition of an individual within the interior of the structure; detecting an ambient condition within the interior of the structure; determining a user activity that is assigned to an area within the interior of the structure where the individual is located; and determining a wellness performance score of the area in response to at least the physiological condition, the ambient condition, and the user activity that is assigned to an area within the interior of the structure where the individual is located.

In addition to one or more of the features described above, or as an alternative, further embodiments may include that the operations further include: adjusting operation of the building system in response to the wellness performance score.

In addition to one or more of the features described above, or as an alternative, further embodiments may include that the operations further include: receiving a user rating from the individual for the area within the interior of the structure where the individual is located, wherein the wellness performance score of the area is determined in response to at least the user rating, the physiological condition, the ambient condition, and the user activity that is assigned to an area within the interior of the structure where the individual is located.

In addition to one or more of the features described above, or as an alternative; further embodiments may include that the operations further include: adjusting operation of the building system in response to the wellness performance score.

In addition to one or more of the features described above, or as an alternative, further embodiments may include that the physiological condition is detected using a wearable physiological sensor worn by the individual.

In addition to one or more of the features described above, or as an alternative, further embodiments may include that the physiological condition is detected using a physiological sensor configured to remotely detect the physiological conditions.

Technical effects of embodiments of the present disclosure include collecting environmental data regarding workstations with an interior of a structure and providing that data to a user to allow the user to better select a workstation within the interior of a structure that is best suited for the type of activity the user would like to undertake.

The foregoing features and elements may be combined in various combinations without exclusivity, unless expressly indicated otherwise. These features and elements as well as the operation thereof will become more apparent in light of the following description and the accompanying drawings. It should be understood, however, that the following description and drawings are intended to be illustrative and explanatory in nature and non-limiting.

BRIEF DESCRIPTION

The following descriptions should not be considered limiting in any way. With reference to the accompanying drawings, like elements are numbered alike:

FIG. 5A is computing device displaying a graphical user interface, in accordance with an embodiment of the disclosure;

FIG. 5B is computing device displaying a graphical user interface, in accordance with an embodiment of the disclosure; and FIG. 5C is computing device displaying a graphical user interface, in accordance with an embodiment of the disclosure.

DETAILED DESCRIPTION

A detailed description of one or more embodiments of the disclosed apparatus and method are presented herein by way of exemplification and not limitation with reference to the Figures.

Figure 1:
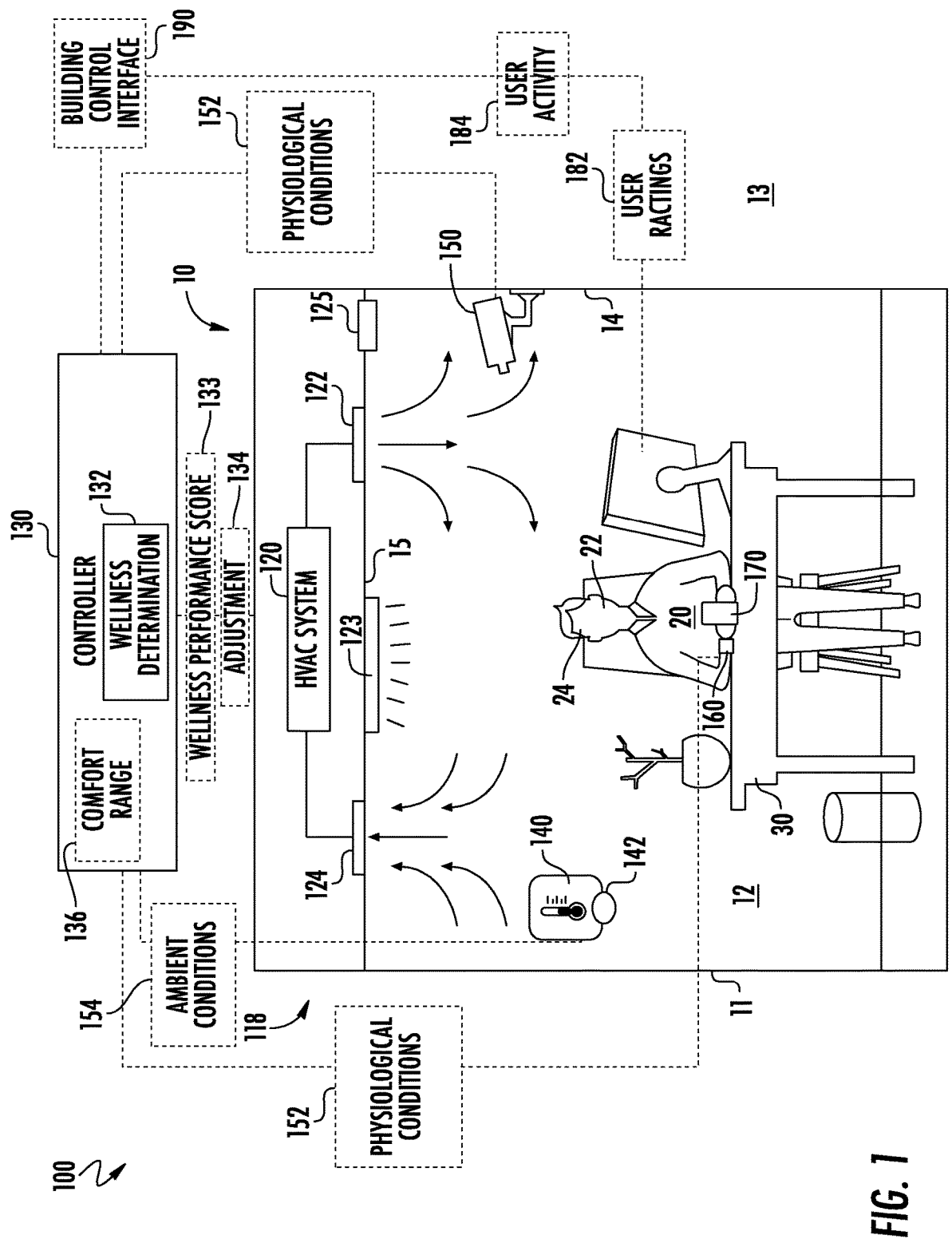
FIG. 1 illustrates a general schematic system diagram of an individual wellness control system, in accordance with an embodiment of the disclosure.

With reference to FIGS. 1, 5A, 5B, and 5C, an individual wellness control system 100 is illustrated in FIG. 1, in accordance with an embodiment of the present disclosure. FIGS. 5A-5C illustrated an interactive application for a mobile device that a user may interact with to view details for various work stations 30 and select/reserve a workstation 30. As will be described below, a building system 118 for a structure is provided. The building system 118 may include, but is not limited to, a heating, ventilation, and air-conditioning (HVAC) 120, a sound masking/attenuation system 125, and a lighting system 123. Human physiological response regulates the heat balance by removing body heat generated by metabolism through various means. Some existing building systems employ space sensors at predefined locations in space within the building premises. The actual human thermal comfort perception may not be in line with temperature figures given by these 'fixed location' space sensors. The actual human light comfort perception may not be in line with light figures given by these 'fixed location' space sensors. So these space sensors do not reflect the comfort felt by the individuals. Embodiments disclosed herein relate to evaluating various operations of the building system to maintain desired environmental conditions in the interior of the structure based in part on the ability of the building system to maintain human physiological comfort.

As seen in FIG. 1, a structure 10 is provided and may be configured as a residence, an industrial building, an office building, a commercial building, a vehicle, a helmet, or a hermetically sealed suit. For purposes of clarity and brevity, however, the following description will relate to the case where the structure 10 is configured as an office building but it is understood that embodiments disclosed herein are not limited to an office building. The structure 10 thus includes a structural body 11 which defines an interior 12 and separates the interior 12 from an exterior 13. The interior 12 may be further divided into multiple rooms and areas for various purposes in the illustrated example of FIG. 1.

The individual wellness control system 100 includes a building system 118, which may include but is not limited to the HVAC system 121, a sound masking/attenuation system 125, and a lighting system 123. The HVAC system 120 is disposed and configured to control ambient conditions 154 within the interior 12. The HVAC system 120 is configured to condition the air within the interior 12 by means of controlling the volume of heated or cooled air supplied to the interior 12. Some examples of a HVAC system 120 may include but are not limited to a forced air system, a heat pump, a fan, a radiator, a fireplace, a pellet stove, a wood stove, a water mister, or any other device known to one of skill in the art to control thermal comfort. The HVAC system 120 may include a return conduit 124 and a supply 122 to aid in the circulation of air within the interior 12. The light system 123 is configured to provide light to a single workstation 30 and/or within the interior 12 of the structural building 11. The brightness and/or color of the light system 123 may be adjusted to be brighter or darker. The sound masking/attenuation system 125 is configured to mask ambient sound proximate a workstation 30, help reduce ambient sound proximate a workstation 30, and/or introduce pleasant ambient sound within the interior 12 of the structural building.

The individual wellness control system 100 also includes a controller 130 configured for controlling comfort of an individual 20 within the interior 12. The controller 130 is in electronic communication with the building system 118 and controls the operations of the building system 118 to provide and maintain a desired thermal environment and comfort level within the interior 12. The electronic communication may be wired and/or wireless. The controller 130 may be an electronic controller including a processor and an associated memory comprising computer-executable instructions that, when executed by the processor, cause the processor to perform various operations. The processor may be but is not limited to a single-processor or multi-processor system of any of a wide array of possible architectures, including field programmable gate array (FPGA), central processing unit (CPU), application specific integrated circuits (ASIC), digital signal processor (DSP) or graphics processing unit (GPU) hardware arranged homogenously or heterogeneously. The memory may be a storage device such as, for example, a random access memory (RAM), read only memory (ROM), or other electronic, optical, magnetic or any other computer readable medium.

The individual wellness control system 100 also includes a system control device 140 (e.g., a thermostat) in electronic communication with the controller 130. The electronic communication between the system control device 140 and the controller 130 may be wired and/or wireless. In a non-limiting embodiment, the system control device 140 may be a mobile application installed on a smart phone. The system control device 140 is generally accessible to an individual 20 and is configured to control various operations of the building system 118 to maintain desired environmental conditions in the interior 12. The system control device 140 may also include a sensor 142 configured to detect ambient conditions 154 in the interior 12, such as, for example, temperature, light, humidity, pressure, noise, luminous flux, and/or any environmental condition known to one of skill in the art.

The following description will also relate to the cases in which the system control device 140 is wirelessly communicative with the controller 130. This is being done for clarity and brevity and is not intended to otherwise limit the scope of the application as a whole. The system control device 140 may have the capability to establish and maintain wireless connectivity over various networks (e.g., Wi-Fi, Bluetooth, Z-Wave, ZigBee, etc.). The system control device 140 can therefore be connected to a local Wi-Fi network and the Internet. This allows the system control device 140 to have additional features and capabilities including, but not limited to, being remotely controllable by a user using the portable computing device (e.g., a mobile phone, a tablet, a laptop, etc.). The system control device 140 may also have a second private wireless communication link operative along any type of network with the controller 130. In addition, the link between the controller 130 and the system control device 140 could be developed to automatically pair and connect.

The individual wellness control system 100 may also include a physiological sensor 150 in electronic communication with the controller 130. The electronic communication between the physiological sensor 150 and the controller 130 may be wired and/or wireless. The physiological sensor 150 is configured to remotely detect (i.e., from a distance) physiological conditions 152 of an individual 20. The physiological conditions 152 of the individual 20 may include but are not limited to heart rate, respiration rate, breathing patterns as an indicator of arousal levels, body temperature as an indicator of thermal comfort, facial expression as an in dictator of emotional and mental state, and eye movement as an indicator of cognitive load, or any other known physiological condition known to one of skill in the art. In one example, the physiological sensor 150 is a thermal imaging camera that captures a facial thermal image (e.g., physiological conditions 152) of the face 22 of the individual 20. The physiological sensor 150 may be configured to visually recognize the forehead region 24 on the face 22 of the individual 20, and capture a facial thermal image of the forehead region 24 of the individual 20 and determined a temperature of the individual 20 in response to the facial thermal image. The physiological sensor 150 is configured to transmit the facial thermal image and/or the temperature as a physiological conditions 152 to the controller 130.

The physiological sensor 150 is positioned in the interior 12 of the structure 10. In a first non-limiting example, the physiological sensor 150 is located on a wall 14 and/or ceiling 15 of a room to capture physiological conditions 152 of multiple individuals 20 in a single room. There may be multiple physiological sensor 150 utilized in the interior. In a second non-limiting example, the physiological sensor 150 may be positioned on a workstation 30 of an individual 20 to capture a physiological conditions 152 of the individual 20 sitting at the workstation 30. For example, the physiological sensor 150 may be positioned on or within a computing device 170. In a third non-limiting example, the physiological sensor 150 may be positioned in a helmet of an individual to capture physiological conditions 152 of the individual 20 wearing the helmet. It is understood that while one individual 20 is illustrated in FIG. 1, the embodiments disclosed herein may be applicable to structures 10 with one or more individuals 20. It is also understood that while one workstation 30 is illustrated in FIG. 1, the embodiments disclosed herein may be applicable to structures 10 with one or more workstations 30 or no workstations 30.

The following description will relate to the cases in which the physiological sensor 150 is wirelessly communicative with the controller 130. This is being done for clarity and brevity and is not intended to otherwise limit the scope of the application as a whole. The physiological sensor 150 may have the capability to establish and maintain wireless connectivity over various networks (e.g., Wi-Fi, Bluetooth, Z-Wave, ZigBee, etc.). The physiological sensor 150 can therefore be connected to a local Wi-Fi network and the Internet. The physiological sensor 150 may also have a second private wireless communication link operative along any type of network with the controller 130. In addition, the link between the controller 130 and the physiological sensor 150 could be developed to automatically pair and connect.

The physiological sensor 150 is configured to transmit the physiological conditions 152 to the controller 130. The controller 130 includes an wellness determination module 132 configured to analyze the performance of the building system 118 and determined a wellness performance score 133. The wellness performance score 133 may be positive if the ambient conditions 154 and/or the physiological conditions 152 are within a comfort range 136. The comfort range 136 may be stored in the controller 130 and may be standard or personalized ranges of ambient conditions 154 and/or physiological conditions 152 where an individual 20 feels comfortable. The comfort range 136 may vary depending on the user's activity, for example focus activity require low level of ambient noise, where as social activity could use medium level of ambient noise. The controller 130 may command an adjustment 134 of the building system 118 in response to the wellness performance score 133.

The individual wellness control system 100 may also include a wearable physiological sensor 160 in electronic communication with the controller 130. The wearable physiological sensor 160 is worn by the individual 20. The wearable physiological sensor 160 is configured to locally detect the physiological conditions of the individual 20, such as, for example, through skin contact with the individual and/or close proximity with the individual 20. The wearable physiological sensor 160 may be a smart watch, a fitness/health tracking computer bracelet, or similar device known to one of skill in the art. The electronic communication between the wearable physiological sensor 160 and the controller 130 is wireless, such as, for example through the internet. The wearable physiological sensor 160 may have the capability to establish and maintain wireless connectivity over various networks (e.g., Cellular, Wi-Fi, Bluetooth, Z-Wave, ZigBee, etc.). The wearable physiological sensor 160 can therefore be connected to a local Wi-Fi network and the Internet. The wearable physiological sensor 160 is configured to detect physiological conditions of the individual 20. The physiological conditions 152 of the individual 20 may include, but are not limited to, heart rate, respiration rate, breathing patterns, galvanic skin response as indicators of the person's arousal levels, body temperature as an indicator of thermal comfort, electroencephalogram and eye movement as an indicator of mental state and cognitive load, or any other known physiological condition known to one of skill in the art. The wearable physiological sensor 160 is configured to transmit the physiological conditions 152 of the individual 20 detected to the controller 130.

The individual wellness control system 100 may also include a computing device 170 in electronic communication with the controller 130. The computing device 170 may be a smart watch, a computer table, a desktop computer, a laptop computer, a smart phone, wearable physiological sensor 160, or a similar device known to one of skill in the art. The electronic communication between the computing device 170 and the controller 130 is wired and/or wireless, such as, for example through the internet. The computing device 170 may have the capability to establish and maintain wireless connectivity over various networks (e.g., Cellular, Wi-Fi, Bluetooth, Z-Wave, ZigBee, etc.).

FIGS. 5A-5C illustrate the computer application for the computing device 170 that generates a graphical user interface 670 via display device 650 for viewing the wellness performance score 133. The computing device 170 may belong to an worker looking for a workstation 30. The computing device 170 may be a desktop computer, laptop computer, smart phone, tablet computer, smart watch, or any other computing device known to one of skill in the art. In the example shown in FIGS. 5A-5C, the computing device 170 is a touchscreen smart phone. The computing device 170 includes an input device 652, such as, example, a mouse, a keyboard, a touch screen, a scroll wheel, a scroll ball, a stylus pen, a microphone, a camera, etc. In the example shown in FIGS. 5A-5C, since the computing device 170 is a touchscreen smart phone, then the display device 650 also functions as an input device 652. FIGS. 5A-5C illustrates a graphical user interface 670 generated on the display device 650 of the computing device 170. A user may interact with the graphical user interface 670 through a selection input, such as, for example, a "click", "touch", verbal command, gesture recognition, or any other input to the user interface 670.

The display device 650 may display a wellness performance score 133 for each workstation 30 within an interior 12 of the structure 10 on a map 200 of the interior 12. Each workstation 30 may be represented by a workstation icon 230 and may be assigned a work station name 232. The workstation icon 230 may be color coded indicating the user activity 184 that was determined for that workstation 30. For example, purple may mean for a focus activity. A specific time available may be displayed for the workstation 30. The user activities 184 may include a social activity, a collaborative activity, a focus activity, or a creative activity. Based on ambient conditions some workstations may be better suited for certain user activities 184 than others. In one example, a quiet and/or well-lit workstation may be more conducive to a focus activity. In another example, a louder and/or darker (i.e., not well-lit) workstation may be more conducive to a social activity. The display device 650 may display information for each workstation broken up by user activity 184, as shown at 680. As illustrated in FIG. 5A each workstation 30 may have a wellness performance score 133 for sunlight and noise. An individual may be able to book a specific workstation 30 for a selected time period 690 via the application on the computing device 170.

The individual 20 is able to submit a user rating 182 and/or a user activity 184 through the computing device 170. The user rating 182 may be feedback submitted by the individual 20 in real-time regarding how comfortable the individual 20 is within the interior 12 of the structure 10 or how suitable the environment is or how well the environment is performing for their user activity 184, such as, for example, there may be ratings in several categories including but not limited to a social activity, a collaborative activity, a focus activity, or a creative activity, as illustrated in FIG. 5C. The user rating 182 may be a star rating (e.g., from zero stars being bad to five stars being good as illustrated in FIG. 5C), a scale rating (e.g., from 1 being bad to 10 being good), a thumbs up or thumbs down, an emoji rating (e.g., emoji indicating hot, emoji indicating cold), or any other rating system known to one of skill in the art. The user may be able to mark location as a favorite or recommend a location. The user activity 184 may be information submitted by the individual 20 in real-time regarding what type of activity the individuals desires (i.e., a desired user activity) to perform within the interior 12 of the structure 10. The user activity may be a social activity, a collaborative activity, a focus activity, or a creative activity. The user rating 182 and the user activity 182 may be submitted to the controller 130 through a building control interface 190. The user activity 184 may be assigned by the controller 130 to the workstation 30 where the individual 20 is located.

Figure 2:
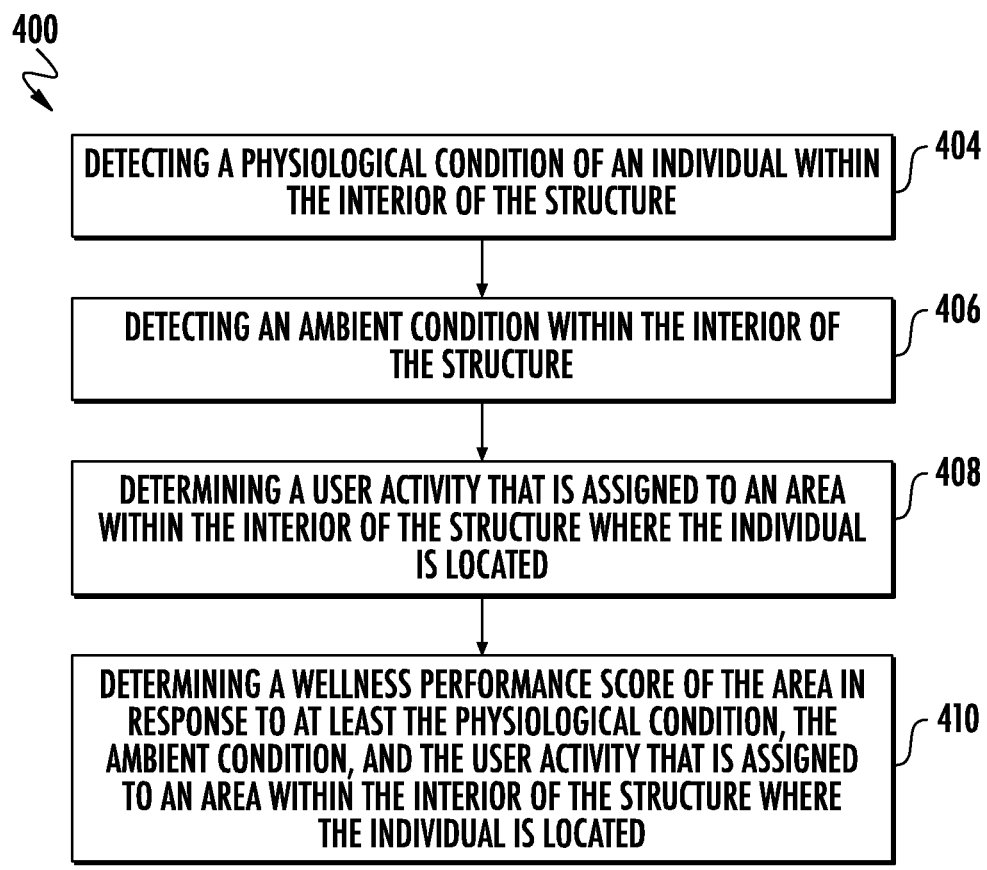
FIG. 2 is a flow diagram illustrating a method of monitoring the individual wellness control system, according to an embodiment of the present disclosure.

Referring now to FIG. 2 with continued reference to FIG. 1. FIG. 2 shows a flow chart of a method 400 of monitoring performance of the building system 118 to control ambient conditions 154 within an interior 12 of a structure 10, in accordance with an embodiment of the disclosure. At block 404, a physiological condition 152 of an individual 20 is detected within the interior 12 of the structure 10. The physiological condition 152 is detected using a wearable physiological sensor 160 worn by the individual 20 and/or using a physiological sensor 150 configured to remotely detect the physiological conditions 152.

At block 406, an ambient condition 154 is detected within the interior 12 of the structure 10. At block 408, a user activity 184 that is assigned to an area within the interior 12 of the structure 10 where the individual 20 is located is determined. An area may be defined as a work area, a workstation 30, a room, an entire floor, or the entire area of the interior.

At block 410, a wellness performance score 133 of the area is determined in response to at least the physiological condition 152, the ambient condition 154, and the user activity 184 that is assigned to an area within the interior 12 of the structure 10 where the individual 20 is located.

The method 400 may also comprise that a user rating 182 is received from the individual 20 for the area within the interior 12 of the structure 10 where the individual 20 is located. Thus, the wellness performance score 133 of the area that is determined in block 410 may be determined in response to at least the user rating 182, the physiological condition 152, the ambient condition 154, and the user activity 184 that is assigned to an area within the interior 12 of the structure 10 where the individual 20 is located.

The method 400 may further comprise that the building system 118 is adjusted in response to the wellness performance score 133. For example, the wellness performance score 133 may indicate that the individual 20 is cold then the HVAC system 120 may be adjusted to provide additional heat to the interior 12. In another example, the wellness performance score 133 may indicate that the individual 20 is hot then the HVAC system 120 may be adjusted to provide additional cooling to the interior 12. In another example, the wellness performance score 133 may indicate that it is too bright for the individual 20 then the lighting system 123 may be adjusted to provide dimmer lighting. In another example, the wellness performance score 133 may indicate that it is too loud for the individual 20 then the sound masking/attenuation system 125 may be adjusted to provide help mask some of the sound.

Figure 4:
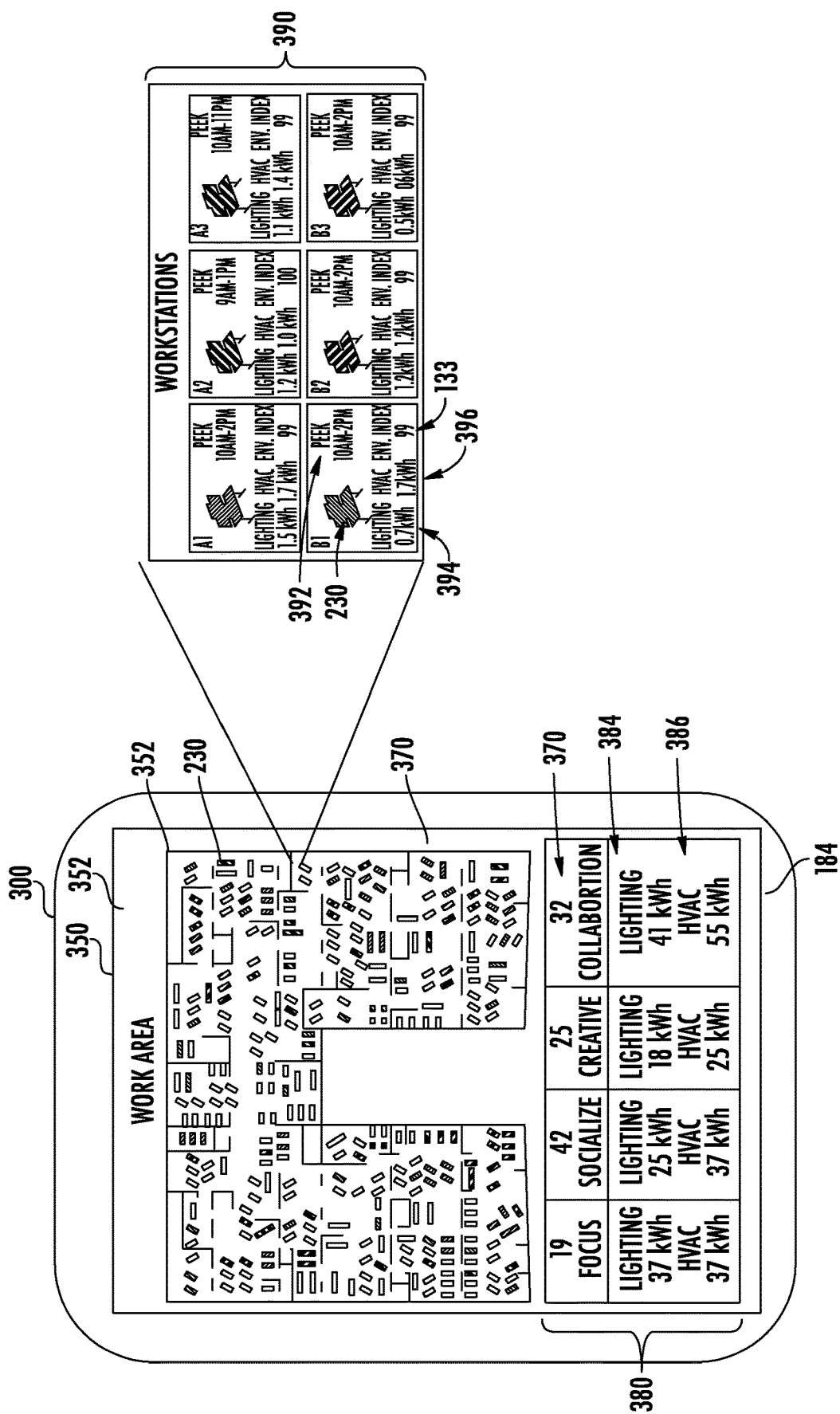
FIG. 4 is computing device displaying a graphical user interface, in accordance with an embodiment of the disclosure.

The method 400 may yet further comprise that the wellness performance score 133 is displayed on a display device. The display device may be a display device 350 of a computing device 300. The computing device 300 of FIG. 4 may be belong to an employee or operator of the building 11 or building system 118. FIG. 4 illustrates a computing device 300 generating a graphical user interface 370 via display device 350 for viewing the wellness performance score 133. The computing device 300 may be a desktop computer, laptop computer, smart phone, tablet computer, smart watch, or any other computing device known to one of skill in the art. In the example shown in FIG. 4, the computing device 300 is a touchscreen smart phone. The computing device 300 includes an input device 352, such as, example, a mouse, a keyboard, a touch screen, a scroll wheel, a scroll ball, a stylus pen, a microphone, a camera, etc. In the example shown in FIG. 4, since the computing device 300 is a touchscreen smart phone, then the display device 350 also functions as an input device 352. FIG. 4 illustrates a graphical user interface 370 generated on the display device 350 of the computing device 300. A user may interact with the graphical user interface 370 through a selection input, such as, for example, a "click", "touch", verbal command, gesture recognition, or any other input to the user interface 370.

The display device 350, through a computer application, may display a wellness performance score 133 for each workstation 30 within an interior 12 of the structure 10 on a map 200 of the interior 12. Each workstation 30 may be represented by a workstation icon 230. The workstation icon 230 may be color coded indicating the user activity 184 that was determined for that area or workstation in block 410. The user activities may include a social activity, a collaborative activity, a focus activity, or a creative activity. Based on ambient conditions some workstations may be better suited for certain user activities 184 than others. In one example, a quiet and/or well-lit workstation may be more conducive to a focus activity. In another example, a louder and/or darker (i.e., not well-lit) workstation may be more conducive to a social activity. The display device 350 may display information for each workstation broken up by user activity 184, as shown at 380. For example, the aggregated average wellness scores of workstation are grouped by each user activity 184 is shown at 382, the estimated power consumption for lighting for each user activity 184 group is shown at 384, and the estimated power consumption HVAC for each user activity 184 group is shown at 386.

The display device 350, through a computer application, may display information for each workstation 30, as shown at 390, which may be a sub-level view of the higher-level view showing the map 200. For example, the peak usage time for each workstation 30 is shown at 392, the estimated power consumption for lighting for each workstation 30 is shown at 394, and the estimated HVAC output for each work station 30 is shown at 396. The display device 350 may display a wellness performance score 133 for each workstation 30 within an interior 12 of the structure 10 on a map 200 of the interior 12 and details for the individual workstations 30 may be displayed as well.

While the above description has described the flow process of FIG. 2 in a particular order, it should be appreciated that unless otherwise specifically required in the attached claims that the ordering of the steps may be varied.

Figure 3:
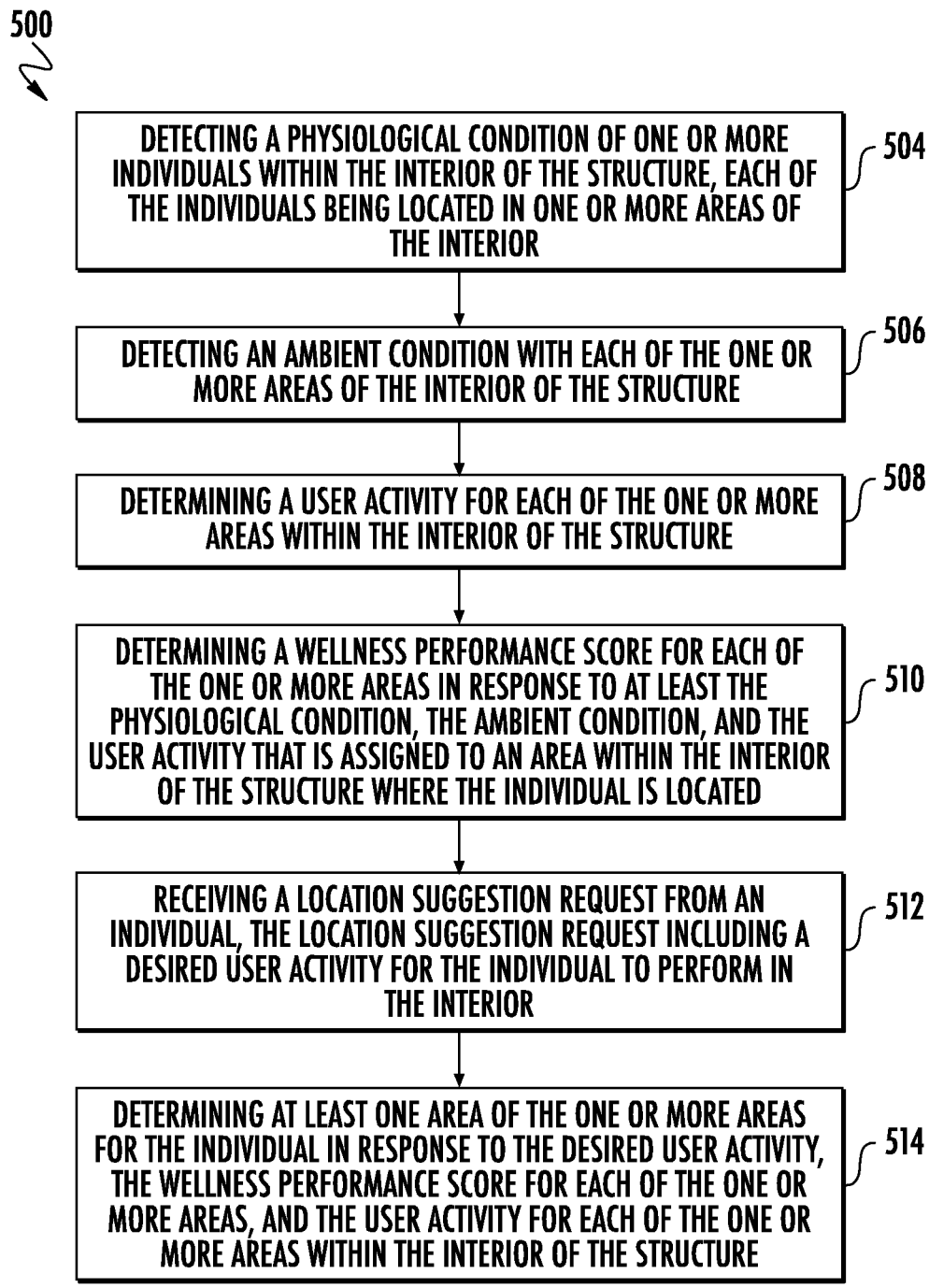
FIG. 3 is a flow diagram illustrating the individual wellness control system, according to an embodiment of the present disclosure.

Referring now to FIG. 3 with continued reference to FIG. 1. FIG. 2 shows a flow chart of a method 500 of monitoring performance of a building system 118 to control ambient conditions 154 within an interior 12 of a structure 10, in accordance with an embodiment of the disclosure.

At block 504, a physiological condition 152 of one or more individuals 20 within the interior 12 of the structure 10, each of the one or more individuals 20 being located in one or more areas of the interior 12. An area may be defined as a work area, a workstation 30, a room, an entire floor, or the entire area of the interior. The physiological condition 152 is detected using a wearable physiological sensor 160 worn by the individual 20 and/or using a physiological sensor 150 configured to remotely detect the physiological conditions 152. At block 506, an ambient condition 154 is detected within each of the one or more areas of the interior 12 of the structure 10.

At block 508, a user activity 508 is determined for each of the one or more areas within the interior 12 of the structure 10. The user activity 508 assigned to the one or more areas may be assigned to a specific workstation 30 in the area and be updated or changed in real time based on the use of the area.

At block 510, a wellness performance score 133 is determined for each of the one or more areas in response to at least the physiological condition 152, the ambient condition 154, and the user activity 184 that is assigned to an area within the interior 12 of the structure 10 where the individual 20 is located.

At block 512, a location suggestion request is received from an individual 20. The location suggestion request including a desired user activity for the individual 20 to perform in the interior 12, such as, for example, a social activity, a collaborative activity, a focus activity, or a creative activity.

At block 514, at least one area of the one or more areas for the individual 20 is determined in response to the desired user activity, the wellness performance score 133 for each of the one or more areas, and the user activity 184 for each of the one or more areas within the interior 12 of the structure 10.

The method 500 may also comprise that a user rating 182 is received from at least one of the one or more individuals 20 for at least one of the one or more areas within the interior 12 of the structure 10. Thus, the wellness performance score of the at least one area of the one or more areas that is determined in block 410 may be determined in response to at least the user rating 182, the physiological condition 152, the ambient condition 154, and the user activity that is assigned to an area within the interior 12 of the structure 10 where the individual 20 is located.

The method 500 may further comprise that the building system 118 is adjusted in response to the wellness performance score 133. For example, the wellness performance score 133 may indicate that an individual 20 is cold then the HVAC system 120 may be adjusted to provide additional heat to the interior 12. In another example, the wellness performance score 133 may indicate that an individual 20 is hot then the HVAC system 120 may be adjusted to provide additional cooling to the interior 12. In another example, the wellness performance score 133 may indicate that it is too bright for the individual 20 then the lighting system 123 may be adjusted to provide dimmer lighting, in another example, the wellness performance score 133 may indicate that it is too loud for the individual 20 then the sound masking/attenuation system 125 may be adjusted to provide help mask some of the sound.

The method 500 may yet further comprise that the wellness performance score 133 is displayed on a display device. The display device may be a display device 350 of a computing device 300. The display device 350 may display a wellness performance score 133 for each workstation 30 within an interior 12 of the structure 10 on a map 200 of the interior. Each workstation 30 may be represented by a workstation icon 230. The workstation icon 230 may be color coded indicating the user activity 184 that was determined for that area or workstation in block 410. The user activities may include a social activity, a collaborative activity, a focus activity, or a creative activity. Based on ambient conditions some workstations may be better suited for certain user activities 184 than others. In one example, a quiet and/or well-lit workstation may be more conducive to a focus activity. In another example, a louder and/or darker (i.e., not well-lit) workstation may be more conducive to a social activity. The display device 350 may display information for each workstation 30 broken up by user activity 184, as shown at 380. For example, the aggregated average wellness scores of workstation are grouped by each user activity 184 is shown at 382, the estimated power consumption for lighting for each user activity 184 group is shown at 384, and the estimated power consumption HVAC for each user activity 184 group is shown at 386

The display device 350 may display information for each workstation 30, as shown at 390, which may be a sub-level view of the higher-level view showing the map 200. For example, the peak usage time for each workstation 30 is shown at 392, the estimated power consumption for lighting for each workstation 30 is shown at 394, and the estimated HVAC output for each work station 30 is shown at 396. The display device 350 may display a wellness performance score 133 for each workstation 30 within an interior 12 of the structure 10 on a map 200 of the interior 12 and details for the individual workstations 30 may be displayed as well.

While the above description has described the flow process of FIG. 3 in a particular order, it should be appreciated that unless otherwise specifically required in the attached claims that the ordering of the steps may be varied.

As described above, embodiments can be in the form of processor-implemented processes and devices for practicing those processes, such as processor. Embodiments can also be in the form of computer program code (e.g., computer program product) containing instructions embodied in tangible media, such as floppy diskettes, CD ROMs, hard drives, or any other non-transitory computer readable medium, wherein, when the computer program code is loaded into and executed by a computer, the computer becomes a device for practicing the embodiments. Embodiments can also be in the form of computer program code, for example, whether stored in a storage medium, loaded into and/or executed by a computer, or transmitted over some transmission medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an device for practicing the exemplary embodiments. When implemented on a general-purpose microprocessor, the computer program code segments configure the microprocessor to create specific logic circuits.

The term "about" is intended to include the degree of error associated with measurement of the particular quantity based upon the equipment available at the time of filing the application.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, hut do not preclude the presence or addition of one or more other features, integers, steps, operations, element components, and/or groups thereof.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. A method of monitoring performance of a building system to control ambient conditions within the interior of a structure, the method comprising:

detecting a physiological condition of one or more individuals within the interior of the structure, each of the one or more individuals being located in one or more areas of the interior;

detecting an ambient condition within each of the one or more areas of the interior of the structure;

determining a user activity for each of the one or more areas within the interior of the structure;

receiving a user rating from at least one of the one or more individuals for at least one of the one or more areas within the interior of the structure;

determining a wellness performance score for each of the one or more areas in response to at least the user rating, the physiological condition, the ambient condition, and the user activity that is assigned to an area within the interior of the structure where the individual is located;

adjusting operation of the building system in response to the wellness performance score;

receiving a location suggestion request from an individual, the location suggestion request including a desired user activity for the individual to perform in the interior; and determining at least one area of the one or more areas for the individual in response to the desired user activity, the wellness performance score for each of the one or more areas, and the user activity for each of the one or more areas within the interior of the structure.

2. The method of claim 1, further comprising:

wherein the wellness performance score of the at least one area of the one or more areas is determined in response to at least the user rating, the physiological condition, the ambient condition, and the user activity that is assigned to an area within the interior of the structure where the individual is located.

3. The method of claim 2, wherein the building system is an HVAC system and the adjusting operation of the building system includes heating or cooling to the one or more areas of the interior.

4. The method of claim 1, wherein the physiological condition is detected using a wearable physiological sensor worn by the individual.

5. The method of claim 1, wherein the physiological condition is detected using a physiological sensor configured to remotely detect the physiological conditions.

6. The method of claim 1, further comprising:

displaying the wellness performance score on a display device.

7. A computer program product embodied on a non-transitory computer readable medium, the computer program product including instructions that, when executed by a processor, cause the processor to perform operations comprising:

detecting a physiological condition of one or more individuals within the interior of the structure, each of the one or more individuals being located in one or more areas of the interior;

detecting an ambient condition within each of the one or more areas of the interior of the structure;

determining a user activity for each of the one or more areas within the interior of the structure;

receiving a user rating from at least one of the one or more individuals for at least one of the one or more areas within the interior of the structure;

determining a wellness performance score for each of the one or more areas in response to at least the user rating, the physiological condition, the ambient condition, and the user activity that is assigned to an area within the interior of the structure where the individual is located;

adjusting operation of the building system in response to the wellness performance score;

receiving a location suggestion request from an individual, the location suggestion request including a desired user activity for the individual to perform in the interior; and determining at least one area of the one or more areas for the individual in response to the desired user activity, the wellness performance score for each of the one or more areas, and the user activity for each of the one or more areas within the interior of the structure.

8. The computer program product of claim 7, wherein the building system is an HVAC system and the adjusting operation of the building system includes heating or cooling to the one or more areas of the interior.

9. The computer program product of claim 7, wherein the operations further comprise:

wherein the wellness performance score of the area is determined in response to at least the user rating, the physiological condition, the ambient condition, and the user activity that is assigned to an area within the interior of the structure where the individual is located.

10. The computer program product of claim 7, wherein the physiological condition is detected using a wearable physiological sensor worn by the individual.

11. The computer program product of claim 7, wherein the physiological condition is detected using a physiological sensor configured to remotely detect the physiological conditions.

* * * * *